United States Patent
Mori et al.

(10) Patent No.: US 6,929,872 B2
(45) Date of Patent: Aug. 16, 2005

(54) ORGANIC ELECTROLUMINESCENT DEVICES

(75) Inventors: Tatsuo Mori, 5-6, Nishihioki 1-chome, Nakagawa-ku, Nagoya-shi, Aichi (JP); Teruyoshi Mizutani, 42-5, Okaue-cho 2-chome, Chikusa-ku, Nagoya-shi, Aichi (JP); Toru Takeda, Fukuoka (JP); Koichi Yamashita, Fukuoka (JP)

(73) Assignees: Nippon Steel Chemical Co., Ltd., Tokyo (JP); Tatsuo Mori, Aichi (JP); Teruyoshi Mizutani, Aichi (JP)

( * ) Notice: Subject to any disclaimer, the term of this patent is extended or adjusted under 35 U.S.C. 154(b) by 0 days.

(21) Appl. No.: 10/398,234
(22) PCT Filed: Oct. 1, 2001
(86) PCT No.: PCT/JP01/08647
§ 371 (c)(1), (2), (4) Date: Aug. 11, 2003
(87) PCT Pub. No.: WO02/30159
PCT Pub. Date: Apr. 11, 2002

(65) Prior Publication Data
US 2004/0028944 A1 Feb. 12, 2004

(30) Foreign Application Priority Data
Oct. 5, 2000 (JP) ........................... 2000-306349
Apr. 24, 2001 (JP) ........................... 2001-126323

(51) Int. Cl.$^7$ ............................................. H05B 33/12
(52) U.S. Cl. .................. 428/690; 428/917; 313/504; 313/506; 252/301.16; 257/40
(58) Field of Search .............................. 428/690, 917; 313/504, 506; 252/301.16; 257/40

(56) References Cited

U.S. PATENT DOCUMENTS

| | | |
|---|---|---|
| 4,536,457 A | 8/1985 | Tam |
| 5,047,687 A | 9/1991 | VanSlyke |

(Continued)

FOREIGN PATENT DOCUMENTS

| | | |
|---|---|---|
| EP | 0 376 311 A2 | 7/1990 |
| JP | 03-078755 A1 | 4/1991 |

(Continued)

OTHER PUBLICATIONS

International Search Report of PCT/JP01/08647 mailed on Dec. 18, 2001.

Primary Examiner—Rena Dye
Assistant Examiner—Camie S. Thompson
(74) Attorney, Agent, or Firm—Rader, Fishman & Grauer PLLC (57) ABSTRACT

This invention relates to highly reliable organic electroluminescent (EL) materials and devices exhibiting high luminance, high light emitting efficiency, minimal deterioration in light emission, usability at high temperature and good storage stability. The organic electroluminescent device of this invention has intermediate layers such as light emitting layer, hole transport layer, hole injection layer and the like arranged between the anode and the cathode and at least one of the intermediate layers comprises a triarylamine derivative represented by general formula (1)

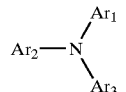

(wherein $Ar_1$–$Ar_3$ are substituted or unsubstituted aryl groups and at least one of $Ar_1$–$Ar_3$ is 9-phenanthryl group represented by general formula (2)); (2)

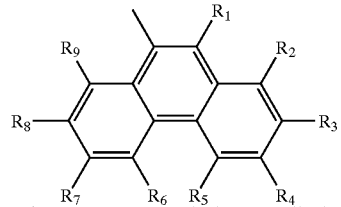

(wherein $R_1$–$R_9$ are H, halogen, alkyl group, aralkyl group, alkenyl group, cyano group, acyl group, alkoxycarbonyl group, alkoxy group or the like).

5 Claims, 2 Drawing Sheets

U.S. PATENT DOCUMENTS

| | | | |
|---|---|---|---|
| 5,219,692 A | * 6/1993 | Shimada et al. | 430/58.65 |
| 5,457,232 A | * 10/1995 | Tanaka et al. | 564/426 |
| 5,554,450 A | * 9/1996 | Shi et al. | 428/690 |
| 6,537,687 B1 | * 3/2003 | Nii | 428/690 |
| 6,572,985 B2 | * 6/2003 | Xie | 428/690 |

FOREIGN PATENT DOCUMENTS

| | | | |
|---|---|---|---|
| JP | 08-199162 A1 | | 8/1996 |
| JP | 09-157643 A1 | | 6/1997 |
| JP | 11-135261 | * | 5/1999 |
| JP | 11-144870 A1 | | 5/1999 |
| JP | 11-312586 A1 | | 11/1999 |

* cited by examiner

ORGANIC ELECTROLUMINESCENT DEVICES

TECHNICAL FIELD OF THE INVENTION

This invention relates to organic electroluminescent devices (also referred to as organic EL devices) which are used in flat light sources and displays.

BACKGROUND TECHNOLOGY

Organic electroluminescent devices are attracting attention as candidates for flat displays of exceptionally high luminance and researches and development works directed to these devices are getting active. An organic electroluminescent device has a structure consisting of a light emitting layer put between two electrodes and a hole injected from the anode and an electron injected from the cathode recombine in the light emitting layer thereby emitting light. Organic materials useful for the devices include low-molecular-weight and high-molecular-weight materials and both materials have proven to yield organic electroluminescent devices of high luminance.

There are two types for such organic electroluminescent devices. One type uses a charge transfer material to which a fluorescent pigment is added as a light emitting layer (C. W. Tang et al., J. Appl. Phys., 65, 3610 (1989)) and the other type uses a fluorescent pigment itself as a light emitting layer (Jpn. J. Appl. Phys., 27, L269 (1988)).

Those organic electroluminescent devices which use a fluorescent pigment itself as a light emitting layer are further divided roughly into three types. The first type has a three-layer structure in which a light emitting layer is put between a hole transport layer and an electron transport layer, the second type has a two-layer structure in which one layer is a laminate of a hole transport layer and a light emitting layer and the third type likewise has a two-layer structure in which one layer is a laminate of an electron transport layer and a light emitting layer. Constructing organic electroluminescent devices in two or three layers has been known to improve the light emitting efficiency.

The electron transport layer in any of the aforementioned organic electroluminescent devices of various structures contains an electron-transmitting compound and performs a function of transmitting electrons injected from the cathode to the light emitting layer. The hole injection layer and the hole transport layer contain hole-transmitting compounds and perform a function of transmitting holes injected from the anode to the light emitting layer. Putting the hole injection layer between the anode and the light emitting layer makes it possible to inject a larger number of holes to the light emitting layer in a lower electric field and, in addition, to confine the electrons injected from the cathode or electron injection layer in the light emitting layer thereby improving the light emitting efficiency and yielding organic electroluminescent devices of excellent light emitting performance.

The performance of these organic luminescent devices, however, has not been satisfactory to warrant practical use. A lack of durability of the materials used for the devices, in particular, poor durability of the hole transport materials, can be cited as the largest obstacle to practical use. The existence of a nonuniform area such as grain boundary in the organic layers of an organic electroluminescent device is likely to cause the electric field to concentrate in this particular area thereby leading to deterioration and destruction of the device. For this reason, the organic layers are frequently used in the amorphous condition. Moreover, an organic electroluminescent device is a device of current injection type and any material to be used for the device is required to have a high glass transition temperature (Tg) because the device in drive deteriorates by the Joule heat if the Tg of the material is low. Another obstacle to practical use has been an unsatisfactory hole transporting performance of the hole transport materials and an impractical light emitting efficiency of the devices.

A large variety of materials, predominantly triphenylamine derivatives, have been known as hole transport materials for the aforementioned organic electroluminescent devices, but few of them are suited for practical use. For example, N,N'-diphenyl-N,N'-bis(3-methylphenyl)-4,4'-diaminobiphenyl (TPD) reported in Appl. Phys. Let., 57, No. 6, p. 531 (1990) was poor in thermal stability and presented a problem regarding the life of devices and the like. Many triphenylamine derivatives are described in U.S. Pat. No. 5,047,687, 4,047,948, 4,536,457, JP 632307(A1), JP 5-234681(A1), JP 5-239455(A1) and JP 8-87122(A1), but none of them has satisfactory properties for practical use.

The starburst amine derivatives described in JP 4-308688 (A1), JP 6-1972(A1) and Adv. Material, 6, p. 677 (1994) and the compounds described in JP 7-126226(A1), JP 8-48656 (A1) and Journal of the Chem. Communication, p. 2175 (1966) do not possess the properties essential for practical use, that is, high light emitting efficiency and long life. Moreover, the use of N,N'-dinaphthyl-N,N'-diphenyl-4, 4'diaminobiphenyl (NPD) is reported in JP 2851185 while the use of derivatives of NPD is reported in JP 9-194441 (A1); an improvement over TPD is described in either case, but even their use did not yield satisfactory hole transport performance and heat resistance.

As noted above, the hole transport materials used in the conventional organic electroluminescent devices do not perform satisfactorily to warrant practical use and there is a demand for enhanced efficiency and longer life for organic electroluminescent devices by the use of improved materials. Furthermore, in the majority of organic electroluminescent devices, light is emitted mostly from the light emitting layer or electron transport layer provided separately from the charge transport layer and rarely from the hole transport layer. One reason for this is the problem of compatibility of the hole transport layer with the simultaneously used electron transport layer, but the factors just as important are the color and intensity of the light emitted by the hole transport material itself. In spite of the expectation that emission of light from the hole transport layer, if possible, would increase the practical value, there are available few such materials. Some of the materials of this kind, represented by the 9-anthryl derivatives described in JP 9-157643(A1), have problems because they emit light of long wavelength and cannot emit light of short wavelength in most cases.

This invention has been made in consideration of the problems associated with the aforementioned conventional technologies and has an object of providing organic electroluminescent devices of high light emitting efficiency and long life and also providing novel compounds, hole transport materials and organic electroluminescent materials useful for said devices.

DISCLOSURE OF THE INVENTION

The inventors of this invention have conducted extensive studies to solve the problems associated with the aforementioned conventional technologies, found that the use of specified triarylamine derivatives can yield electroluminescent devices of high efficiency and long life and completed this invention.

This invention relates to an organic electroluminescent device prepared by using a triarylamine derivative represented by general formula (1).

(1)

In formula (1), $Ar_1$, $Ar_2$ and $Ar_3$ are independently phenyl group, phenyl group containing a lower alkyl substituent, phenyl group containing a lower alkoxy substituent, cyanophenyl group, phenoxyphenyl group, halophenyl group, naphthyl group, naphthyl group containing a lower alkyl substituent, naphthyl group containing a lower alkoxy substituent, cyanonaphthyl group, halonaphthyl group, fluorenyl group, carbazolyl group, carbazolyl group containing a lower alkyl substituent, biphenylyl group, biphenylyl group containing a lower alkyl substituent, biphenylyl group containing a lower alkoxy substituent, thiophenyl group, indolyl group, pyridyl group or 9-phenanthryl group represented by general formula (2) and at least one of $Ar_1$, $Ar_2$ and $Ar_3$ is the 9-phenanthryl group.

(2)

In formula (2), $R_1$–$R_9$ are independently hydrogen, halogen, alkyl group, aralkyl group, alkenyl group, cyano group, acyl group, alkoxycarbonyl group, alkoxy group, alkylsulfonyl group or haloalkyl group.

This invention further relates to the triarylamine derivatives represented by formula (1) in which at least two of $Ar_1$, $Ar_2$ and $Ar_3$ are 9-phenanthryl groups represented by the aforementioned general formula (2). Still further, this invention relates to an organic electroluminescent device having a light emitting layer and a hole transport layer or hole injection layer with any one of the aforementioned triarylamine derivatives incorporated in any one of said light emitting layer, hole transport layer or hole injection layer.

This invention will be described in detail below.

The groups $Ar_1$, $Ar_2$ and $Ar_3$ in the triarylamines represented by general formula (1) in this invention are substituted or unsubstituted aryl groups and at least one or two of them are 9-phenanthryl groups represented by general formula (2). The triarylamines of this invention containing at least two 9-phenanthryl groups represented by general formula (2) are novel compounds.

The substituted or unsubstituted aryl groups other than 9-phenanthryl group include phenyl, ethylphenyl, biphenylyl, methylbiphenylyl, ethylbiphenylyl, cyclohexylbiphenylyl, terphenylyl, chlorophenyl, nitrophenyl, cyanophenyl, o-, m- and p-methoxyphenyl, methylthiophenyl, o-, m- and p-fluorophenyl, dichlorophenyl, dicyanophenyl, trifluoromethoxyphenyl, o-, m- and p-tolyl, o-, m- and p-cumenyl, mesityl, phenoxyphenyl, (α, α-dimethylbenzyl)phenyl, (N,N-dimethyl)aminophenyl, (N,N-diphenylamino)phenyl, pentalenyl, indenyl, naphthyl, methylnaphthyl, azulenyl, heptalenyl, acenaphthylenyl, phenalenyl, fluorenyl, anthraquinolyl, methylanthryl, phenanthryl, triphenylenyl, pyrenyl, chrysenyl, ethylchrysenyl, picenyl, perylenyl, chloroperylenyl, pentaphenyl, pentacenyl, tetraphenylenyl, hexaphenyl, hexacenyl, rubicenyl, coronenyl, trinaphthlenyl, heptaphenyl, heptacenyl, pyranthrenyl, ovalenyl, fluorenyl and carbazolyl. Preferable groups are phenyl, phenyl containing a lower alkyl substituent, phenyl containing a lower alkoxy substituent, cyanophenyl, phenoxyphenyl, halophenyl, naphthyl, naphthyl containing a lower alkyl substituent, naphthyl containing a lower alkoxy substituent, cyanonaphthyl, halonaphthyl, fluorenyl, carbazolyl, carbazolyl containing a lower alkyl substituent, biphenylyl, biphenylyl containing a lower alkyl substituent, indolyl and pyridyl. Lower alkyl and lower alkoxy substituents in some of the aforementioned groups preferably contain 1–5 carbon atoms. More preferable groups are one- to three-membered aryl groups selected from phenyl, naphthyl and phenathrenyl groups or from said groups further substituted with one to three, preferably one, lower alkyl groups containing three or less carbon atoms, lower alkoxy groups containing three or less carbon atoms, cyano groups, phenoxy groups, phenyl groups or halogen.

The groups $R_1$–$R_9$ in general formula (2) are independently hydrogen, halogen, alkyl, aralkyl, alkenyl, cyano, acyl, alkoxycarbonyl, alkylsulfonyl or haloalkyl. Preferred are hydrogen, halogen and alkyl groups containing three or less carbon atoms.

According to this invention, the compounds represented by formula (1) can be prepared, for example, by the following method.

Substituted or unsubstituted 9-iodophenanthrene is subjected to a substitution reaction with a substituted or unsubstituted arylamine or a substituted or unsubstituted diarylamine in nitrobenzene as solvent in the presence of potassium carbonate and a copper catalyst.

A triarylamine derivative containing one 9-phenanthryl group can be synthesized by the reaction of substituted or unsubstituted 9-iodophenanthrene with a substituted or unsubstituted secondary diarylamine derivative in a solvent in the presence of a base and a catalyst. A triarylamine derivative containing two 9phenanthryl groups can be synthesized by the reaction of one equivalent of a primary arylamine with two equivalents of substituted or unsubstituted 9-iodophenanthrene in a solvent in the presence of a base and a catalyst. Moreover, a triarylamine derivative containing three 9-phenanthryl groups can be synthesized by the reaction of one equivalent of substituted or unsubstituted 9-aminophenanthrene with two equivalents of substituted or unsubstituted 9-iodophenanthrene in a solvent in the presence of a base and a catalyst.

The bases useful for the aforementioned synthesis include inorganic bases such as potassium carbonate, lithium hydroxide and sodium hydroxide and organic bases such as pyridine, picoline and triethylamine. The catalysts useful for this synthesis include copper powder, copper oxide, copper halides and copper sulfate. The solvents useful for the synthesis include any compound which dissolves the raw materials and allows the reaction to proceed, for example, toluene, xylene, nitrobenzene, dimethyl sulfoxide and N,N-dimethylformamide.

Typical examples of those triarylamine derivatives which are used in organic electroluminescent devices of this invention are listed in the following tables 1–5, but this invention is not limited to these examples. It is to be understood that $Ar_3$ is 9-phenanthryl group. The triarylamine derivatives containing two or more 9phenanthryl groups correspond to Compound No. 32 and those shown thereafter.

TABLE 1

| Compd. No. | Ar₁ | Ar₂ |
|---|---|---|
| 1 |  |  |
| 2 |  |  |
| 3 |  |  |
| 4 |  |  |
| 5 |  |  |
| 6 |  |  |
| 7 |  |  |
| 8 |  |  |
| 9 |  |  |
| 10 |  |  |
| 11 |  |  |
| 12 |  |  |

TABLE 1-continued

| Compd. No. | Ar₁ | Ar₂ |
|---|---|---|
| 13 |  |  |
| 14 |  |  |
| 15 |  |  |

TABLE 2

| Compd. No. | Ar₁ | Ar₂ |
|---|---|---|
| 16 |  |  |
| 17 |  |  |
| 18 |  |  |
| 19 |  |  |
| 20 |  |  |
| 21 |  |  |
| 22 |  |  |

TABLE 2-continued

| | | |
|---|---|---|
| 23 |  |  |
| 24 |  |  |
| 25 |  |  |
| 26 |  |  |
| 27 |  |  |
| 28 |  |  |

TABLE 3

| | | |
|---|---|---|
| 29 |  |  |
| 30 |  |  |
| 31 |  |  |
| 32 |  |  |
| 33 |  |  |

TABLE 3-continued

| | | |
|---|---|---|
| 34 |  |  |
| 35 |  |  |
| 36 |  |  |
| 37 |  |  |
| 38 |  |  |
| 39 |  |  |
| 40 |  |  |

TABLE 4

| | | |
|---|---|---|
| 41 |  |  |
| 42 |  |  |

TABLE 4-continued

TABLE 5

TABLE 5-continued

251

252

The triarylamine derivatives to be used in this invention have a rigid phenanthryl group in their structure with the resultant high glass transition temperature and melting point. This in turn improves the resistance (heat resistance) to the Joule heat to be generated in the organic layers, between the organic layers or between the organic layer and the metal electrode during electroluminescence as well as the resistance to the high temperature environment. Hence, the use of the triarylamine derivatives in the hole transport layer or as a light emitting material, host material for the light emitting layer and doping material for the light emitting layer in organic electroluminescent devices is advantageous as it helps to emit light of high luminance and allow the emission of light to last longer. This effect can be improved still further by the use of those triarylamine derivatives which contain two or more rigid 9-phenanthryl groups.

In general, a compound to be used in one of the organic layers constituting an organic electroluminescent device preferably does not form an excited complex with a compound to be used in another layer and the triarylamine derivatives of this invention advantageously form excited complexes with other compounds with difficulty. This probably results from the introduction of the phenanthryl group. The organic electroluminescent devices of this invention not only function with high efficiency but also exhibit good durability during storage and drive. This is due to a high Tg of the triarylamine derivatives used in this invention. The triarylamine derivatives represented by formula (1) can also function as materials for hole transport, hole injection and emission of light.

A variety of structures are possible for the organic electroluminescent devices of this invention, but the fundamental structure is the one in which at least one organic layer containing the aforementioned triarylamine derivative is put between the cathode (A) and the anode (C). A plurality of intermediate layers such as hole injection layer (B1), hole transport layer (B2), organic light emitting layer (B3), electron transport layer (B4), hole blocking layer (B5) and electron injection layer (B6) are provided between the cathode (A) and the anode (C). An organic layer containing the aforementioned triarylamine derivative occupies at least one of the aforementioned intermediate layers, preferably at least one of the hole injection layer (B1), hole transport layer (B2) and organic light emitting layer (B3). As needed, it is possible to add other materials for hole injection, hole transport, hole blocking, light emission, electron injection and electron transport to the organic layer containing the aforementioned triarylamine derivative. For example, in the case where the triarylamine derivative in question is used in the light emitting layer, the addition of other light emitting materials to this light emitting layer can emit light of a different wavelength or improve the light emitting efficiency.

Concrete structures of organic electroluminescent devices include the following laminated structures:
1) (A)/(B3)/(C), 2) (A)/(B2)/(B3)/(C), 3) (A)/(B2)/(B3)/(B5)/(C),
4) (A)/(B1)/(B2)/(B3)/(C), 5) (A)/(B1)/(B2)/(B3)/(B5)/(C),
6) (A)/(B3)/(B4)/ (C), 7) (A)/(B3)/(B4)/ (B6) /(C),
8) (A)/(B3)/(B5)/(B4)/(B6)/(C), 9) (A)/(B2)/(B3)/(B5)/(B4)/(C),
10) (A) /(B1)/(B2)/(B3)/(B4)/(C), 11) (A)/ (B1)/ (B2)/(B3)/(B4)/(B5)/ (C)
12) (A)/(B1)/(B2)/(B3)/(B4)/(B6)/(C), and
13) (A)/(B1)/(B2)/(B3)/(B5)/(B4)/(B6)/(C).

The hole injection layer (B1), electron injection layer (B6) and hole blocking layer (B5) are not always necessary, but providing these layers can improve the light emitting efficiency.

The organic electroluminescent device of this invention is preferably supported by a substrate, regardless of which of the aforementioned structures it assumes. The substrate here is satisfactory if it has acceptable mechanical strength, thermal stability and transparency and, for example, glass or transparent plastic film may be used as substrate. Useful as materials for the anode of the organic electroluminescent devices of this invention are those which have a work function of larger than 4 eV such as metals, alloys, electrically conductive compounds and mixtures thereof. Concrete examples are metals such as Au and electrically conductive transparent materials such as CuI, indium tin oxide (ITO), $SnO_2$ and ZnO.

Materials useful for the cathode are those having a work function of smaller than 4 eV such as metals, alloys, electrically conductive compounds and mixtures thereof. Concrete examples are Ca, Mg, Li, Al, magnesium alloy, lithium alloy and aluminum alloy. Examples of the alloys are Al/Li, Mg/Ag and Mg/In. In order to take out light from an organic electroluminescent device efficiently, at least one of the electrodes preferably has a light transmission of 10% or more. The sheet resistance of the electrode is preferably made several hundreds of Ω/mm or less. The film thickness, although it depends on the properties of the electrode material, is normally chosen to be in the range from 10 nm to 1 μm, preferably from 10 to 400 nm. An electrode such as this can be fabricated by vapor deposition or sputtering of the aforementioned electrode materials.

The triarylamine derivatives of this invention contain a tertiary arylamine group in the molecule and, because of this, they have a capability of transporting holes and are suitable for hole transport materials. Still more, they can be laminated to other hole transport materials than those of this invention and used as electron transport materials.

The materials to be used in the hole injection layer are required to satisfy the conditions that they have a good contact with the anode, they can be formed into thin uniform film and they are thermally stable, that is, they have a high melting point or Tg or a melting point of 250° C. or above and a Tg of 100° C. or above. The triarylamine derivatives of this invention satisfy these requirements and are suitable as hole injection materials.

Moreover, the triarylamine derivatives of this invention can also be used as light emitting materials because of their highly intensive fluorescence in the state of thin film. In this case, it is preferable to laminate a hole blocking material as occasion demands. Such hole blocking material can be selected from known ones; for example, the oxadiazole derivatives and triazole derivatives described in Jpn. J. Appl.

Phys., 32, L917 (1993), the phenanthroline derivatives described in MRS 98 Spring Meeting, G2.1, April 1998, and the hole blocking materials described in JP 11-329734(A1). The thickness of a layer containing the triarylamine derivatives of this invention is normally in the range of 5–300 nm, preferably 10–100 nm. A thin film with a thickness of this order can preferably be prepared by vapor deposition or, if necessary, the triarylamine derivative is mixed with a binder resin, dissolved in a solvent, applied to a substrate by spin coating and the like and dried to form a film.

Other hole injection materials and hole transport materials to be used in the organic electroluminescent devices of this invention may be selected suitably from the charge transfer materials for holes customarily used in the area of photoconductive materials or from the materials publicly known for the hole injection layer and hole transport layer in organic electroluminescent devices. For example, they include carbazole derivatives (N-phenylcarbazole, polyvinylcarbazole and the like), triarylamine derivatives (TPD), polymers containing aromatic tertiary amines in the main or side chain, 1,1-bis(4-di-p-tolylaminophenyl)cyclohexane, N,N'-diphenyl-N,N'-dinaphthyl-4,4'-diaminobiphenyl, 4,4', 4"-tris[N-(3-methylphenyl)-N-phenylamino] triphenylamine, the compounds described in Journal of the Chem. Communication, p. 2175 (1996), the compounds described in JP 57-144558(A1), JP 61-62038(A1), JP 61-124949(A1), JP-61-134354(A1), JP 61-134355(A1), JP 61-112164(A1), JP 4-308688(A1), JP 6-312979(A1), JP 6-267658(A1), JP 7-90256(A1), JP 7-97355 (A1), JP 7-97355(A1), JP 6-1972(A1), JP 7-126226(A1), JP 7-126615(A1), JP 8-100172(A1) and JP 8-48656(A1), the starburst amine derivatives described in Advanced Material, 6, p. 677 (1994), the stilbene derivatives described in Advance Papers (II) of the 72nd Spring Annual Meeting of the Chemical Society of Japan, p. 1392, 2PB098, phthalocyanine derivatives (metal-free phthalocyanine, copper phthalocyanine, etc.) and polysilanes. In the organic electroluminescent devices of this invention, the materials to be used for hole injection, hole transport, light emission and electron injection preferably have a Tg of 80° C. or above, more preferably 100° C. or above.

The hole injection layer and the hole transport layer in the organic electroluminescent devices of this invention may be laminates of a plurality of layers containing one kind or more of the aforementioned compounds.

Other electron injection and electron transport materials to be used in the organic electroluminescent devices of this invention are not restricted in any specific manner and they may be selected from those electron transport compounds which have been customarily used in the area of photoconductive materials or from those materials which are publicly used in the electron injection and electron transport layers in organic electroluminescent devices. Preferable examples of such electron transport compounds are LiF, aluminum-8-hydroxyquinoline complex (Alq3) and its derivatives, the diphenylquinone derivatives (Journal of the Society of Electrophotography of Japan, 30, 3 (1991)), the perylene derivatives (J. Appl. Phys., 27, 269 (1988) and elsewhere), the oxadiazole derivatives (the preceding literature, Jpn. J. Appl. Phys., 27, L713 (1988), Appl. Phys. Lett., 55, 1489 (1989) and elsewhere), the thiophene derivatives (JP 4-212286(A1) and elsewhere), the triazole derivatives (Advance Papers (III) of the 43rd Symposium of the Society of Polymer Science, Japan, Pla007 and elsewhere), the metal complexes of oxine derivatives (Technical Research Reports of the Institue of Electronics, Information and Communication Engineers, 92 (311), 43 (1992) and elsewhere) and the phenanthroline derivatives (Advance Papers of the 43rd Symposium of the Society of Polymer Science, Japan, 14J07 and elsewhere).

As for other light emitting materials useful for the light emitting layer in the organic electroluminescent devices of this invention, known light emitting materials such as the daylight fluorescent materials, fluorescent brighteners, laser pigments, organic scintillators, and a variety of reagents for fluorometry described in "Photofunctional Materials," p. 236 (1991) in Polymer Functional Material Series, edited by the Society of Polymer Science, Japan and published by Kyoritsu Shuppan Co., Ltd. in addition to Alq3 and its derivatives. Concrete examples of preferred materials are polycyclic condensed compounds such as anthracene, pyrene, chrysene, perylene, coronene, rubrene and quinacridone, oligophenylene compounds such as quaterphenyl, scintillators for liquid scintillation such as 1,4-bis(2- methylstyryl)benzene, 1,4-bis(4-methyl-5-phenyl-2-oxazolyl)benzene, 1,4-bis(5-phenyl-2-oxazolyl) benzene, 2,5-bis(5-tert-butyl-2-benzoxazolyl)thiophene, 1,4-diphenyl-1,3-butadiene, 1,6-diphenyl-1,3,5-hexatriene and 1,1,4,4-tetraphenyl-1,3-butadiene, the metal complexes of oxine derivatives described in JP 63-264692(A1), coumarin dyes, dicyanomethylenepyran dyes, dicyanomethylenethiopyran dyes, polymethine dyes, oxobenzanthracene dyes, xanthene dyes, carbostyryl dyes and perylene dyes, the oxazine compounds described in DE patent 2534713, the stilbene derivatives described in Advance Papers of the 40th Meeting of the Society of Applied Physics, 1146 (1993), the spiro compounds described in JP 7-278537(A1) and the oxadiazole compounds described in JP 4-363891(A1).

The layers constituting the organic electroluminescent devices of this invention can be formed respectively by making a thin film from the material constituting the respective layer by a known technique such as vapor deposition, spin coating and ink jet printing. The thickness of the film formed in this manner is not restricted and can be selected in consideration of the properties of the material to be used. Normally, the film thickness falls in the range of 2–5,000 nm. As for the method of making a thin film of a given triphenylamine derivative, it is preferable to apply the technique of vapor deposition which forms a uniform film with ease and generates pinholes with difficulty. In making a thin film by vapor deposition, the conditions vary with the kind of phenanthrene derivative and the target crystalline structure and association structure of the LB film, but they are preferably selected in the following range: the temperature for heating a boat, 50–400° C.; the degree of vacuum, 1–10 Pa; the rate of vapor deposition, 0.01–50 nm/sec; the temperature of a substrate, from −150° C. to +300° C.; the film thickness, from 5 nm to 5 $\mu$m.

The preparation of an organic electroluminescent device by the use of a phenanthrene derivative of this invention is explained below by citing the preparation of an organic electroluminescent device with a structure of the aforementioned anode/phenanthrene derivative layer/cathode as an example. A thin film of the material for the anode is formed by vapor deposition on a suitable substrate in a thickness of 1$\mu$m or less, preferably in the range of 10–200 nm, then a thin film of the phenanthrene derivative is formed on the anode to form a light emitting layer, and finally a thin film of the material for the cathode is formed by vapor deposition on the light emitting layer in a thickness of 1$\mu$m or less. In the aforementioned preparation of the organic electroluminescent device, it is also possible to reverse the sequence and form the cathode, the light emitting layer and the anode in this order.

A direct current is applied to the organic electroluminescent device thus prepared while keeping the anode + and the cathode − and, on application of a voltage of 2–40 V, light emission can be observed from the side of the transparent or translucent electrode (anode and/or cathode). This organic electroluminescent device also emits light on application of an alternating current voltage. The wave form of the alternating current to be applied is optional.

PREFERRED EMBODIMENTS OF THE INVENTION

This invention will be described in further detail with reference to the synthetic examples and examples and it is not limited to the description in the following examples as long as it does not depart from its subject matter.

Synthetic Example 1
Synthesis of N,N-di(9-phenanthryl)aniline (No. 32)

To 50 ml of nitrobenzene were added 6.69 g (0.022 mole) of 9-iodophenanthrene, 0.93 g (0.010 mole) of aniline, 2.12 g of $K_2CO_3$ and 1.67 g of copper powder and the mixture was allowed to react at 180° C. for 27 hours in an atmosphere of nitrogen. Upon completion of the reaction, the reaction mixture was discharged into 200 ml of methanol, the separated dark brown product was dissolved in chloroform, the solution was stripped of the solvent by distillation and the product was washed with methanol. Thereafter, the product was purified by column chromatography by the use of silica gel and further purified by sublimation to give 2.98 g (0.0067 mole, 67%) of Compound 32 in white powder. This compound was submitted to proton nuclear magnetic resonance spectrometry ($^1$H-NMR; solvent, $CDCl_3$), mass spectrometry (m/e) and differential scanning calorimetry for measurement of melting point or Tg and the results were as follows.

$^1$H-NMR: δ ($CDCl_3$) 6.88–6.97 (m, 3 H), 7.16 (dd, J=7.6, 8.8 Hz, 2H), 7.44–7.66 (m, 12H), 8.22 (dd, J=0.8, 8.4 Hz, 2H), 8.67 (dd, J=8.4 Hz, 2H), 8.74 (dd, J=8.4 Hz, 2H)

m/e: 445 ($M^+$)

m.p.: 295° C.

Synthetic Example 2
Synthesis of N,N-di(9-phenanthryl)-2-toluidine (No. 33)

To 50 ml of nitrobenzene were added 6.69 g (0.022 mole) of 9-iodophenanthrene, 1.07 g (0.010 mole) of o-toluidine, 2.12 g of $K_2CO_3$ and 1.67 g of copper powder and the mixture was allowed to react at 180° C. for 27 hours in an atmosphere of nitrogen. Upon completion of the reaction, the reaction mixture was discharged into 200 ml of methanol, the separated dark brown product was dissolved in chloroform, the solution was stripped of the solvent by distillation and the product was washed with methanol. Thereafter, the product was purified by column chromatography by the use of silica gel and further purified by sublimation to give 3.58 g (0.0078 mole, 78%) of Compound 33 in white powder.

$^1$H-NMR: 1.54 (s, 3H), 6.38 (d, J=7.6 Hz, 1H), 6.62 (brs, 1H), 6.83 (brm, 2H), 7.32 (d, J=4.0 Hz, 2H), 7.55–7.72 (m, 11H), 8.06 (d, J=7.6 Hz, 1H), 8.78 (dd, J=8.4, 18.8 Hz, 2H), 8.84 (d, J=8.0 Hz, 2H)

m/e: 459 ($M^+$)

m.p.: 252° C.

Tg: 105° C.

Synthetic Example 3
Synthesis of N,N-di(9-phenanthryl)-3-toluidine (No. 34)

To 50 ml of nitrobenzene were added 6.69 g (0.022 mole) of 9-iodophenanthrene, 1.07 g (0.010 mole) of m-toluidine, 2.12 g of $K_2CO_3$ and 1.67 g of copper powder and the mixture was allowed to react at 180° C. for 27 hours in an atmosphere of nitrogen. Upon completion of the reaction, the reaction mixture was discharged into 200 ml of methanol, the separated dark brown product was dissolved in chloroform, the solution was stripped of the solvent by distillation and the product was washed with methanol. Thereafter, the product was purified by column chromatography by the use of silica gel and further purified by sublimation to give 4.09 g (0.0089 mole, 89%) of Compound 34 in white powder.

$^1$H-NMR: 2.16 (s, 3H), 6.68 (d, J=7.2 Hz, 1H), 6.75 (m, 2H), 7.03 (t, J=7.6 Hz, 1H), 7.44–7.65 (m, 12H), 8.23 (d, J=7.2 Hz, 2H), 8.67 (d, J=8.0 Hz, 2H), 8.74 (d, J=8.4 Hz, 2H)

m/e: 445 ($M^+$)

m.p.: 351 ° C.

Synthetic Example 4
Synthesis of N,N-di(9-phenanthryl)-4-toluidine (No. 35)

To 50 ml of nitrobenzene were added 6.69 g (0.022 mole) of 9-iodophenanthrene, 1.07 g (0.010 mole) of p-toluidine, 2.12 g of $K_2CO_3$ and 1.67 g of copper powder and the mixture was allowed to react at 180° C. for 27 hours in an atmosphere of nitrogen. Upon completion of the reaction, the reaction mixture was discharged into 200 ml of methanol, the separated dark brown product was dissolved in chloroform, the solution was stripped of the solvent by distillation and the product was washed with methanol. Thereafter, the product was purified by column chromatography by the use of silica gel and further purified by sublimation to give 3.86 g (0.0084 mole, 84%) of Compound 35 in white powder.

$^1$H-NMR: 2.28 (s, 3H), 6.81 (d, J=8.4 Hz, 2H), 6.97 (d, J=8.4 Hz, 2H), 7.41–7.51 (m, 6 H), 7.56–7.64 (m, 6H), 8.22 (d, J=7.6 Hz, 2H), 8.66 (d, J=8.4 Hz, 2H), 8.72 (d, J=8.4 Hz, 2H)

m/e: 445 ($M^+$)

m.p.: 245° C.

Synthetic Example 5
Synthesis of N,N-di(9-phenanthryl)-2-anisidine (No. 36)

To 50 ml of nitrobenzene were added 6.69 g (0.022 mole) of 9-iodophenanthrene, 1.23 g (0.010 mole) of o-anisidine, 2.12 g of $K_2CO_3$ and 1.67 g of copper powder and the mixture was allowed to react at 180° C. for 27 hours in an atmosphere of nitrogen. Upon completion of the reaction, the reaction mixture was discharged into 200 ml of methanol, the separated dark brown product was dissolved in chloroform, the solution was stripped of the solvent by distillation and the product was washed with methanol. Thereafter, the product was purified by column chromatography by the use of silica gel and further purified by sublimation to give 3.61 g (0.0076 mole, 76%) of Compound 36 in white powder.

$^1$H-NMR: 3.12 (s, 3H), 6.39 (m, 1H), 6.49 (m, 1H), 6.59–6.62 (m, 2H), 6.78 (m, 2H), 7.56–7.76 (m, 8H), 8.24 (dd, J=0.8, 8.0 Hz, 2H), 8.77–8.86 (m, 4H)

m/e: 475 ($M^+$)

m.p.: 268° C.

Synthetic Example 6
Synthesis of N,N-di(9-phenanthryl)-3-anisidine (No. 37)

To 50 ml of nitrobenzene were added 6.69 g (0.022 mole) of 9-iodophenanthrene, 1.23 g (0.010 mole) of m-anisidine, 2.12 g of $K_2CO_3$ and 1.67 g of copper powder and the mixture was allowed to react at 180° C. for 27 hours in an atmosphere of nitrogen. Upon completion of the reaction, the reaction mixture was discharged into 200 ml of methanol, the separated dark brown product was dissolved in chloroform, the solution was stripped of the solvent by distillation and the product was washed with methanol. Thereafter, the product was purified by column chromatography by the use of silica gel and further purified by sublimation to give 4.12 g (0.0088 mole, 88%) of Compound 37 in white powder.

$^1$H-NMR: 3.59 (s, 3H), 6.49 (m, 3H), 7.06 (t, J=8.0 Hz, 1H), 7.46–7.64 (m, 12H), 8.23 (dd, J=0.8, 8.4 Hz, 2H), 8.67 (d, J=8.4 Hz, 2H), 8.73 (d, J=8.0 Hz, 2H)

m/e: 475 ($M^+$)

m.p.: 321° C.

Synthetic Example 7
Synthesis of N,N-di(9-phenanthryl)-4-anisidine (No. 38)

To 50 ml of nitrobenzene were added 6.69 g (0.022 mole) of 9-iodophenanthrene, 1.23 g (0.010 mole) of p-anisidine, 2.12 g of $K_2CO_3$ and 1.67 g of copper powder and the mixture was allowed to react at 180° C. for 27 hours in an atmosphere of nitrogen. Upon completion of the reaction, the reaction mixture was discharged into 200 ml of methanol, the separated dark brown product was dissolved in chloroform, the solution was stripped of the solvent by distillation and the product was washed with methanol. Thereafter, the product was purified by column chromatography by the use of silica gel and further purified by sublimation to give 3.85 g (0.0081 mole, 81%) of Compound 38 in white powder.

$^1$H-NMR: 3.76 (s, 3H), 6.74 (d, J=9.2 Hz, 2H), 6.90 (d, J=8.8 Hz, 2H), 7.39–7.41 (m, 4H), 7.50 (m, 2H), 7.55–7.61 (m, 6H), 8.22 (dd, J=1.2, 8.4 Hz, 2H), 8.65 (d, J =8.0 Hz, 2H), 8.72 (d, J=8.0 Hz, 2H)

m/e: 445 ($M^+$)

Tg: 122 ° C.

Synthetic Example 8
Synthesis of N,N-di(9-phenanthryl)-3-fluorophenylamine (No. 47)

The reaction and the subsequent purification were carried out as in Synthetic Example 1 except using 1.11 g (0.010 mole) of m-fluoroani line in place of the aniline to give 3.38 g (0.0073 mole, 73%) of Compound 47 in light yellow powder.

$^1$H-NMR: 6.50–6.55 (brm, 2H), 7.06 (dd, J=6.4, 7.6 Hz, 2H), 7.47–7.68 (m, 12H), 8.20 (dd, J=0.8, 8.4 Hz, 2H), 8.68 (d, J=8.0 Hz, 2H), 8.75 (d, J=8.0 Hz, 2H)

m/e: 463 ($M^+$)

m. p.: 307° C.

Tg: 119° C.

Synthetic Example 9
Synthesis of N,N-di(9-phenanthryl)-2,3-dimethylphenylamine (No. 244)

The reaction and the subsequent purification were carried out as in Synthetic Example 1 except using 1.21 g (0.010 mole) of 2,3-dimethylaniline in place of the aniline to give 2.98 g (0.0063 mole, 63%) of Compound 244 in light yellow powder.

$^1$H-NMR: 1.63 (s, 3H), 2.09 (s, 3H), 6.31 (d, J=8.4 Hz, 1H), 6.58 (brm, 1H), 6.72 (br, 1H), 7.31 (m, 3H) , 7.53–7.73 (m, 10H), 8.03 (m, 1H), 8.76–8.85 (m, 4H)

m/e: 473 ($M^+$)

Tg: 107° C.

Synthetic Example 10
Synthesis of N,N-di(9-phenanthryl)-3,5-dimethylphenylamine (No. 245)

The reaction and the subsequent purification were carried out as in Synthetic Example 1 except using 1.21 g (0.010 mole) of 3,5-dimethylaniline in place of the aniline to give 2.93 g (0.0062 mole, 62%) of Compound 245 in light yellow powder.

$^1$H-NMR: 2.11 (s, 6H), 6.53 (s, 2H), 6.60 (s, 2H), 7.41–7.65 (m, 12H), 8.22 (dd, J–1.2, 8.4 Hz, 2H), 8.67 (d, J=8.4 Hz, 2H), 8.43 (d, J=8.4 Hz, 2H)

m/e: 473 ($M^+$)

Tg: not detected

Synthetic Example 11
Synthesis of N,N-di(9-phenanthryl)-3,4-dimethylphenylamine (No. 246)

The reaction and the subsequent purification were carried out as in Synthetic Example 1 except using 1.21 g (0.010 mole) of 3,4-dimethylaniline in place of the aniline to give 3.03 g (0.0064 mole, 64%) of Compound 246 in light yellow powder.

$^1$H-NMR: 2.07 (s, 3H), 2.19 (s, 3H), 6.62 (dd, J=1.2, 8.4 Hz, 1H), 6.76 (d, J=2.0 Hz, 1H), 6.90 (d, J=8.0 Hz, 1H), 7.43–7.64 (m, 12H), 8.23 (d, J=8.4 Hz, 2H), 8.67 (d, J=8.4 Hz, 2H), 8.72 (d, J=8.4 Hz, 2H)

m/e: 473 ($M^+$)

m.p.: 270° C.

Tg: 138° C.

Synthetic Example 12
Synthesis of N,N-di(9-phenanthryl)-2,5-dimethylphenylamine (No. 249)

The reaction and the subsequent purification were carried out as in Synthetic Example 1 except using 1.21 g (0.010 mole) of 2,5-dimethylaniline in place of the aniline to give 2.41 g (0.0051 mole, 51%) of Compound 249 in light yellow powder.

$^1$H-NMR: 1.59 (s, 3 H), 2.01 (s, 3H), 6.21 (d, J=1.6 Hz, 1H), 6.44 (d, J=4.4 Hz, 1H) , 6.71 (d, J=6.8 Hz, 1H), 7.34 (d, J=4.4 Hz, 3H), 7.50–7.76 (m, 10H), 8.07 (d, J=8.4 Hz, 1H), 8.76 (d, J=8.4 Hz, 2H), 8.85 (dd, J=8.0, 13.6 Hz, 2H)

m/e: 473 ($M^+$)

Tg: 109° C.

Synthetic Example 13
Synthesis of N,N-di(9-phenanthryl)-2,4-dimethylphenylamine (No. 250)

The reaction and the subsequent purification were carried out as in Synthetic Example 1 except using 1.21 g (0.010 mole) of 2,4-dimethylaniline in place of the aniline to give 2.79 g (0.0059 mole, 63%) of Compound 250 in light yellow powder.

$^1$H-NMR: 1.68 (s, 3H), 2.13 (s, 3H), 6.31 (d, J=8.0 Hz, 1H), 6.63 (d, J=7.6 Hz, 1H), 6.69 (s, 1H), 7.28–7.33 (m, 3H) , 7.50–7.75 (m, 10H) , 8.02 (d, J=8.4 Hz, 1H), 8.81 (m, 4H)

m/e: 473 ($M^+$)

Tg: 107 ° C.

Synthetic Example 14
Synthesis of N,N-di(9-phenanthryl)-3,4-dimethoxyphenylamine (No. 251)

The reaction and the subsequent purification were carried out as in Synthetic Example 1 except using 1.53 g (0.010 mole) of 3,4-dimethoxyaniline in place of the aniline to give 2.58 g (0.0051 mole, 51%) of Compound 251 in light yellow powder.

$^1$H-NMR: 3.60 (s, 3H), 3.83 (s, 3H), 6.40 (dd, J=2.4, 8.4 Hz, 1H), 6.64 (m, 2H), 7.25–7.64 (brm, 12H), 8.18–8.30 (br, 2H), 8.67 (d, J=7.6 Hz, 2H), 8.72 (d, J=8.0 Hz, 2H)

m/e: 505 (M$^+$)

Tg: 132° C.

Synthetic Example 15

Synthesis of N,N-di(9-phenanthryl)-3,5-dimethoxyphenylamine (No. 252)

The reaction and the subsequent purification were carried out as in Synthetic Example 1 except using 1.53 g (0.010 mole) of 3,5-dimethoxyaniline in place of the aniline to give 2.58 g (0.0051 mole, 51%) of Compound 251 in light yellow powder.

$^1$H-NMR: 3.55 (s, 6H), 6.04 (s, 2H), 6.08 (s, 1H), 7.23–7.65 (m, 12H), 8.22 (dd, J=0.8, 8.4 Hz, 2H), 8.65 (d, J=8.0 Hz, 2H), 8.72 (d, J=8.4 Hz, 2H)

m/e: 505 (M$^+$)

Tg: 118° C.

Examples 1–15

Figure 1:
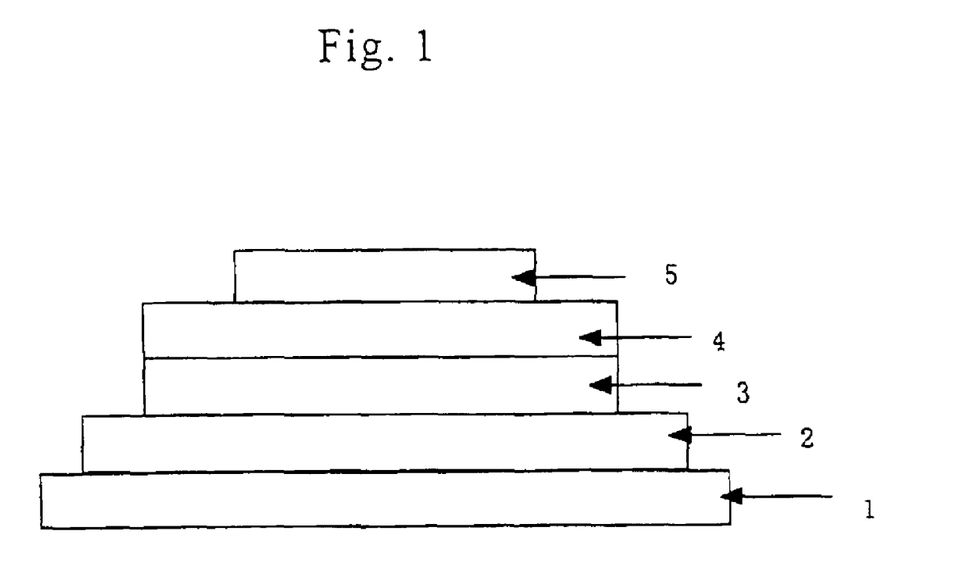
FIG. 1 is a schematic cross section of an organic electroluminescent device.
Figure 2:
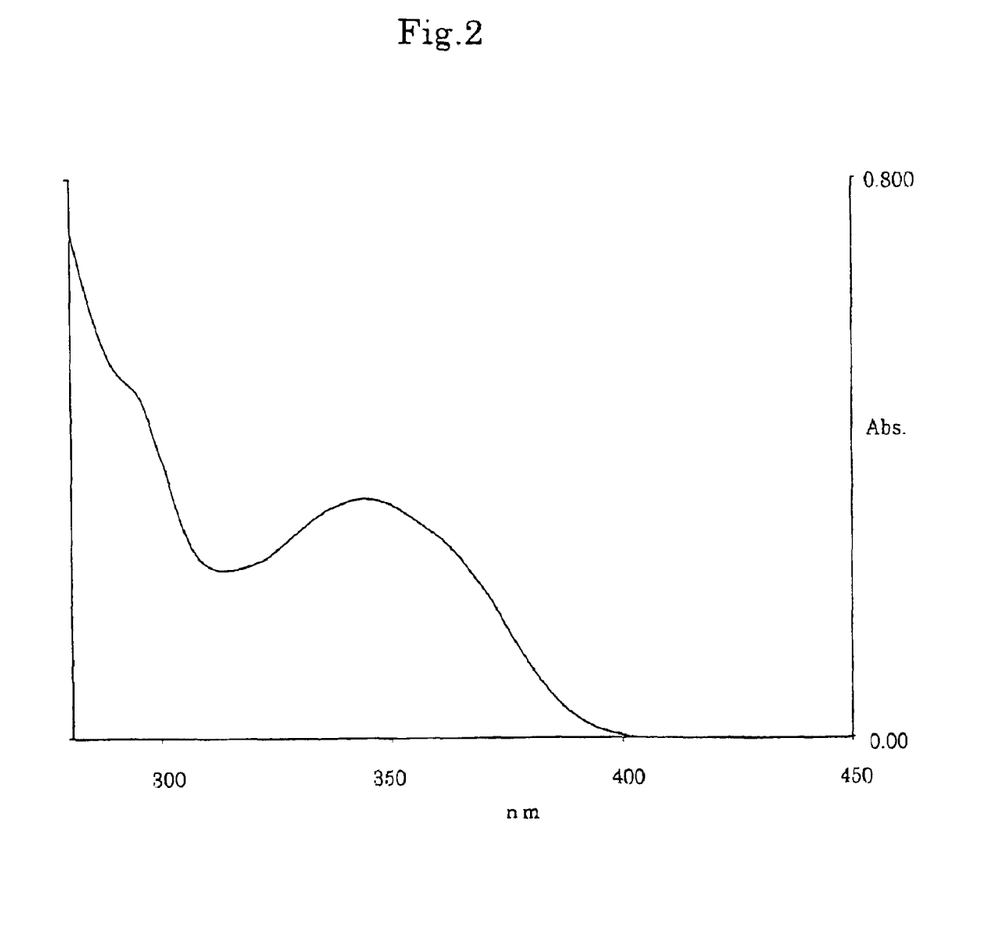
FIG. 2 is a UV chart determined on Compound 35.

An organic electroluminescent device with a layered structure shown in FIG. 1 was prepared as follows.

By the use of a vapor deposition equipment of resistance heating type, fifteen kinds of compounds (Examples 1–15) were respectively deposited in a thickness of 50 nm on clean ITO electrode 2/glass substrate 1 with a resistivity of 15Ω/□ and an electrode area of 2×2 mm$^2$ (available from Sanyo Vacuum Industries, Co., Ltd.) to form a hole transport layer 3 while controlling the rate of vapor deposition by a film thickness controller of quartz oscillator type available from Ulvac and setting the degree of vacuum at (7–9)×10$^{-5}$ Pa. Following this, Alq3 as light emitting material was deposited on the hole transport layer 3 in the same vapor deposition equipment without breaking the vacuum to form a light emitting layer 4. Finally, LiF and Al were deposited on the light emitting layer 4, while maintaining the vacuum, in a thickness of 6 Å and 20 nm respectively to form a cathode 5.

The electroluminescent device thus prepared was connected to an outside power source and a direct current voltage was applied to the device; it was confirmed that the devices all possessed the light emitting characteristics shown in Table 6. It was further confirmed that all the devices emitted green light with the peak wavelength appearing at 514 nm and light was emitted from Alq3 alone.

Comparative Examples 1–2

Electroluminescent devices were prepared as in Example 1 by the use of known hole transport materials or TPD and NPD. Their light emitting characteristics are shown in Table 6.

TABLE 6

| | Hole transport material | Color of emitted light | Voltage for initial light emission 1 cd/m$^2$ (V) | Maximum luminance (cd/m$^2$) | Current density at luminance of 1,000 cd/m$^2$ (mA/cm$^2$) |
|---|---|---|---|---|---|
| Comparative example 1 | TPD | Green | 4.5 | 18,000 | 43 |
| 2 | NPD | Green | 5.0 | 16,000 | 46 |
| Example 1 | Compound 32 | Green | 5.0 | 17,500 | 50 |

TABLE 6-continued

| | Hole transport material | Color of emitted light | Voltage for initial light emission 1 cd/m$^2$ (V) | Maximum luminance (cd/m$^2$) | Current density at luminance of 1,000 cd/m$^2$ (mA/cm$^2$) |
|---|---|---|---|---|---|
| 2 | Compound 33 | Green | 5.1 | 17,000 | 52 |
| 3 | Compound 34 | Green | 6.0 | 16,000 | 46 |
| 4 | Compound 35 | Green | 4.5 | 18,000 | 44 |
| 5 | Compound 36 | Green | 5.0 | 16,000 | 51 |
| 6 | Compound 37 | Green | 5.0 | 16,000 | 48 |
| 7 | Compound 38 | Green | 6.0 | 16,000 | 46 |
| 8 | Compound 47 | Green | 5.3 | 14,500 | 44 |
| 9 | Compound 244 | Green | 5.8 | 17,000 | 48 |
| 10 | Compound 245 | Green | 6.0 | 18,000 | 55 |
| 11 | Compound 246 | Green | 5.9 | 16,000 | 59 |
| 12 | Compound 249 | Green | 5.8 | 16,000 | 49 |
| 13 | Compound 250 | Green | 5.7 | 17,000 | 53 |
| 14 | Compound 251 | Green | 5.9 | 15,000 | 52 |
| 15 | Compound 252 | Green | 6.1 | 16,000 | 51 |

Examples 16–30

The heat-resistant properties of the aforementioned compounds were evaluated as follows. The respective compound alone was vapor-deposited on a glass substrate in a thickness of 1000 Å in the manner described in Example 1. Thereafter, the deposited film was stored at 20° C. and 30% humidity and observed visually to find the number of days required for the thin film to crystallize. The results are shown in Table 7.

Examples 3–4

The heat resistant properties of TPD and NPD are shown as comparative examples in Table 7.

TABLE 7

| | Compound | Number of days required for crystallization |
|---|---|---|
| Comparative example 3 | TPD | 7 |
| 4 | NPD | 25 |
| Example 16 | Compound 32 | 31 |
| 17 | Compound 33 | 32 |
| 18 | Compound 34 | 40 |
| 19 | Compound 35 | 36 |
| 20 | Compound 36 | 33 |
| 21 | Compound 37 | 42 |
| 22 | Compound 38 | 31 |
| 23 | Compound 47 | 31 |
| 24 | Compound 244 | 36 |
| 25 | Compound 245 | 45 |
| 26 | Compound 246 | 48 |
| 27 | Compound 249 | 34 |
| 28 | Compound 250 | 36 |
| 29 | Compound 251 | 48 |
| 30 | Compound 252 | 42 |

Example 31

On the ITO/glass electrode used in Example 1–3 was vapor-deposited NPD as hole transport material in a thickness of 50 nm to form a hole transport layer. A light emitting layer was formed on the hole transport layer by vapor-depositing Compound 32 as light emitting material in a thickness of 50 nm. Following this, bathocuproin (BCP) represented by formula (3) was vapor-deposited on the light emitting layer in a thickness of 30 nm to serve as a hole blocking layer and on this layer was vapor-deposited deposited Alq3 in a thickness of 50 nm as an electron transport layer. Further vapor deposition of LiF in a thickness of 6 Å and Al in a thickness of 20 nm formed a cathode. The device thus prepared has the following structure: ITO/hole transport layer (NPD)/light emitting layer (Compound 32)/hole blocking layer (BCP)/electron transport layer (Alq3)/cathode (LiF/Al).

This electroluminescent device was connected to an outside power source and a direct current voltage was applied to the device; light emitted was not green light from the Alq3 used as an electron transport layer but blue light from Compound 32 used as light emitting material. This device showed good storage stability as it suffered no marked rise in driving voltage and no loss in light emitting efficiency and luminance after storage for a long period of time.

(3)

Example 32

A device was prepared as in Example 31 by replacing the light emitting material with Compound 35. When the device was connected to an outside power source and a direct current voltage was applied, blue light was emitted from the light emitting material as in Example 31. This device also showed good storage stability with no marked rise in driving voltage and no loss in light emitting efficiency and luminance after storage for a long period of time.

Industrial Applicability

The triarylamine derivatives of this invention are materials useful for organic electroluminescent devices. This invention can provide organic electroluminescent devices with high light emitting efficiency and good durability because of the use of specified triarylamine derivatives. The triarylamine derivatives of this invention perform excellently as hole transport materials, organic light emitting materials and the like.

What is claimed is:

1. A triarylamine derivative represented by general formula (1)

(1)

wherein $Ar_1$, $Ar_2$ and $Ar_3$ are independently phenyl group, phenyl group containing a lower alkyl substituent, phenyl group containing a lower alkoxy substituent, cyanophenyl group, phenoxyphenyl group, halophenyl group, naphthyl group, naphthyl group containing a lower alkyl substituent, naphthyl group containing a lower alkoxy substituent, cyanonaphthyl group, halonaphthyl group, fluorenyl group, carbazolyl group, carbazolyl group containing a lower alkyl substituent, biphenylyl group, biphenylyl group containing a lower alkyl substituent, biphenylyl group containing a lower alkoxy substituent, thiophenyl group, indolyl group, pyridyl group or 9-phenanthryl group represented by general formula (2) and at least two of $Ar_1$, $Ar_2$ and $Ar_3$ are 9-phenanthryl groups represented by general formula (2);

(2)

wherein $R_1$–$R_9$ are independently hydrogen, halogen, alkyl group, cyano group, acyl group, alkoxycarbonyl group, alkoxy group, alkylsulfonyl group, or haloalkyl group.

2. An organic electroluminescent device prepared by using the triarylamine derivative described in claim 1.

3. An organic electroluminescent device as described in claim 2, wherein the device has a light emitting layer and said light emitting layer comprises the triarylamine derivative.

4. An organic electroluminescent device as described in claim 2, wherein the device has a hole transport layer and said hole transport layer comprises the triarylamine derivative.

5. An organic electroluminescent device comprising an anode, a cathode, and an organic electroluminescent material layer between the anode and cathode, wherein at least one organic electroluminescent material layer comprises the triarylamine derivative as described in claim 1.

* * * * *